United States Patent [19]

Karol

[11] Patent Number: 5,177,213
[45] Date of Patent: Jan. 5, 1993

[54] SUCCINATE DERIVATIVES OF 2,5-DIMERCAPTO-1,3,4-THIADIAZOLES

[75] Inventor: Thomas J. Karol, Norwalk, Conn.

[73] Assignee: R. T. Vanderbilt Company, Inc., Norwalk, Conn.

[21] Appl. No.: 383,126

[22] Filed: Jul. 20, 1989

[51] Int. Cl.$^5$ .................. C07D 285/112; C10M 1/48
[52] U.S. Cl. ..................................... 548/142; 252/47.5
[58] Field of Search ................. 548/142; 252/475

[56] References Cited

U.S. PATENT DOCUMENTS

| | | | |
|---|---|---|---|
| 2,836,564 | 5/1958 | Roberts et al. | 252/47.5 |
| 3,980,573 | 9/1976 | Okorodudo | 548/142 |
| 4,107,168 | 8/1978 | Okorududu | 260/302 E |
| 4,410,703 | 10/1983 | Okorududu | 548/142 |

OTHER PUBLICATIONS

Liston, "Lubricant Additives-What They Are and How They Function," The Vortex, 8-17 (1984).
Kirk-Othmer, Encyclopedia of Chemical Technology, Third Ed., 11, John Wiley & Sons, New York, 480-484 (1980).
Kirk-Othmer, Ibid, 19, 252 (1982).

*Primary Examiner*—Robert Gerstl
*Attorney, Agent, or Firm*—Rasma B. Balodis

[57] ABSTRACT

Disclosed are novel succinic acid derivatives of 2(and 5)-2-hydroxyethylthio)-1,3,4-thiadiazole. These compounds are shown to be effective multifunctional additives for improving the anticorrosion and performance characteristics of lubricants and alcohol-based fuels.

5 Claims, No Drawings

SUCCINATE DERIVATIVES OF 2,5-DIMERCAPTO-1,3,4-THIADIAZOLES

BACKGROUND OF THE INVENTION

The present invention concerns novel derivatives of thiadiazole compounds and their use as functional additives for lubricating compositions and alcohol fuel. More particularly the novel thiadiazoles are derived from 2,5-dimercapto-1,3,4-thiadiazole and succinic acid or anhydride.

Lubricants which are used for heavy duty service such as maintenance of diesel engines, internal combustion engines and the like contain a variety of additives to prevent their deterioration during use and to improve the overall performance of the lubricant. These additives can cause excessive wear of special components of the engine due to chemical reactions between the additive and the metal. Particularly detrimental are sulfur-containing additives which are widely used as antioxidants and antiwear agents. The sulfur compounds tend to corrode those metal parts which contain copper, bronze, silver and other sulfur-reactive metals.

It has been now discovered that certain succinate derivatives of 1,3,4-thiadiazole function as antioxidants and antiwear agents as well as corrosion inhibitors when used in lubricating compositions. Furthermore, the novel succinate derivatives display corrosion inhibition and antiwear functionality in alcohol fuel. It is desirable to add such additives to alcohol fuel to control corrosion and ring bore wear.

SUMMARY OF THE INVENTION

The present invention provides novel succinate derivatives of 1,3,4-thiadiazole characterized by the structural formula $$R^5-O-\overset{O}{\underset{\|}{C}}-CH_{(1-2)}\overset{R^3}{\underset{|}{C}}H_{(1-2)}-\overset{O}{\underset{\|}{C}}-O-\overset{R^1}{\underset{|}{C}}H-CH_2-S-\overset{N-N}{\underset{S}{C}}\overset{\|}{\underset{}{C}}-S-R \quad (I)$$

wherein R represents hydrogen, alkyl, alkenyl, cycloalkyl, alkylcycloalkyl, 2-hydroxyalkyl and a group of the structural formula $$-CH_2-\overset{R^2}{\underset{|}{C}}H-O-\overset{O}{\underset{\|}{C}}-CH_{(1-2)}\overset{R^4}{\underset{|}{C}}H_{(1-2)}-\overset{O}{\underset{\|}{C}}-O-R^6$$

and wherein $R^1$, $R^2$, $R^3$ and $R^4$ may be selected independently from the group consisting of alkyl, aralkyl, cycloalkyl, aryl, alkaryl, alkenyl and alkynyl groups, $R^5$ and $R^6$ may be selected independently from the group consisting of hydrogen, metal cation and trialkylammonium.

Another aspect of the invention concerns oil-based and water-based lubricating compositions containing the novel compounds of formula (I) in an amount sufficient to impart multifunctional properties.

It is a further object of the invention to provide alcohol fuel compositions containing the novel compounds of formula (I) in an amount sufficient to impart antiwear and corrosion inhibiting properties.

DESCRIPTION OF SPECIFIC EMBODIMENTS

The reaction products of the invention may be prepared by reacting 2,5-dimercapto-1,3,4-thiadiazole with one or two molar equivalents of an epoxy compound to form the corresponding alcohol derivative. Then esters may be formed by esterification with succinic acid or anhydride.

The general reaction scheme is illustrated by the following equation wherein 2,5-dimercapto-1,3,4-thiadiazole is reacted with one mole of ethylene oxide to form the corresponding alcohol and then esterified with succinic acid.

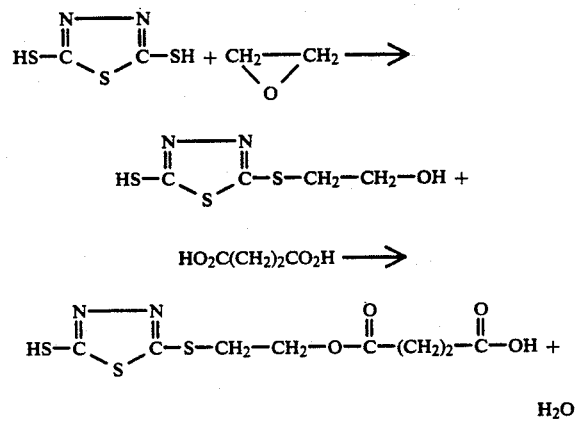

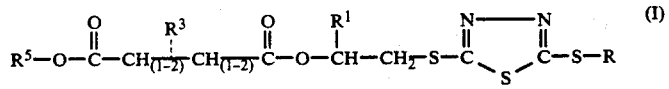

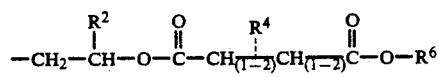

$$H_2O$$

Preferably, the reaction may be conducted in the presence of an inert solvent such as, toluene and benzene and a reaction promoter as for example tertiary amines. The reaction temperature will depend upon the specific reactants and solvent media employed. Typically reaction temperatures range from about 20° C. to 140° C. The reaction illustrated by the equation is the preferred method. Other methods of synthesis may be used.

The R group in formula I may be selected from hydrogen, alkyl, alkenyl, cycloalkyl, 2-hydroxyalkyl and succinate ester derivative. The alkyl group may contain 1 to 100 carbon atoms and may have a straight or branched chain. It may be substituted by aryl, alkenyl or alkynyl groups. The cycloalkyl groups contemplated herein may have 6 to 14 carbon atoms and may be substituted by an alkyl group.

The groups $R^1$ and $R^2$ in formula I may be the same or different. Similarly, $R^3$ and $R^4$ may be the same or different. The groups $R^1$ to $R^4$ may be selected from alkyl, cycloalkyl, aryl, alkaryl, alkenyl and alkynyl groups. The alkyl groups may have 1 to 50 carbon atoms arranged in a straight or branched chain. The alkyl groups may be polymeric in nature as for example polymeric residues of alpha-olefins. The alkyl groups may be substituted by aryl, alkenyl or alkynyl groups. The cycloalkyl groups may have 6 to 14 carbon atoms and may be substituted by alkyl or polymeric alkyl chains.

The thiadiazole derivatives of the invention are useful as lubricating additives. The novel compounds possess multifunctional properties. In particular the compounds function as antioxidants, antiwear agents and corrosion inhibitors when incorporated into lubricating compositions. Succinic acid derivatives substituted by a polymeric residue also possess dispersant properties.

The lubricating compositions contemplated herein include lubricating oils and lubricating greases containing a major amount of base oil. The base oil may be selected from oils derived from petroleum hydrocarbon and synthetic sources. The hydrocarbon base oil may be selected from naphthenic, aromatic, and paraffinic mineral oils. The synthetic oils may be selected from, among others, alkylene polymers, polysiloxanes, carboxylic acid esters and polyglycol ethers.

Another lubricating composition useful herein includes water-based systems. Typically the aqueous systems comprise at least 40 percent of water and zero to less than 15 percent of base oil. Oil-soluble additives are incorporated in the system with the aid of solubilizer/stabilizer systems. The water based systems are useful not only as lubricants, but also as functional fluids such as cutting oils, hydraulic fluids, and transmission fluids.

Other compositions useful herein are alcohol fuels. The fuels are blends of unleaded gasoline and lower aliphatic alcohols such as methanol, ethanol, 2-methyl-1-propanol, methyl 2-methyl-2-propyl ether and the like. These fuels have a tendency of phase separation upon contamination with small amounts of water and consequently cause corrosion of the metal parts of the engine. The compounds of the invention are useful for inhibiting corrosion of alcohol based fuels. In addition, the compounds impart antiwear properties to the fuel.

The amount of the thiadiazole additive required to be effective for imparting improved multifunctional characteristics in the lubricating compositions may range from about 0.1 to 12 percent and preferably from about 0.1 to 5.0 percent based on the weight of the composition. The fuel compositions may contain from about 0.01 to 2.0 percent of the thiadiazole additive. The preferred range is about 0.01 to 0.5 percent of the additive of the total composition.

The lubricating and fuel compositions may contain the necessary ingredients to prepare the composition as for example dispersing agents, emulsifiers and viscosity improvers. Greases may be prepared by addition of thickeners, as for example salts and complexes of fatty acids, polyurea compounds, clays and quaternary ammonium bentonite. Depending on the intended use of the lubricant, other functional additives may be added to enhance a particular property of the lubricant. The compositions may further contain known antioxidants, extreme pressure agents, metal passivators, rust inhibitors and other antiwear agents. The fuel compositions may further contain phase separation inhibitors, antiknock agents and octane improvers.

The following examples are given for the purpose of further illustrating the invention. All percentages and parts are based on weight unless otherwise indicated.

EXAMPLE 1

2,5-Bis(2-hydroxyethylthio)-1,3,4-thiadiazole (25.08 g, 0.105 mol), dodecenylsuccinic anhydride (56.72 g, 0.213 mol) and diluent oil (27.3 g) were charged in a reaction vessel. The reaction was carried out under nitrogen at 120° to 130° C. with stirring for 1.5 hours. The product was filtered while hot.

EXAMPLE 2

The product of Example 1 (42.3 g) and copper oxide (5.3 g) were charged to a reaction vessel and heated at 110° to 120° C. for 1 hour. The produced copper salt was filtered while hot.

EXAMPLE 3

2,5-Bis(butoxymethyl-2-hydroxyethylthio)-1,3,4-thiadiazole (108.9 g, 0.27 mol) and dodecenylsuccinic anhydride (157.19 g, 0.59 mol) were charged to a reaction vessel and heated with stirring at 130° to 135° C. for 1 hour. The product was filtered while hot.

EXAMPLE 4

2,5-Bis(2-methyl-2-hydroxyethylthio)-1,3,4-thiadiazole (39.34 g, 0.147 mol) and dodecenylsuccinic anhydride (81.74 g, 0.307 mol) were charged to a reaction vessel and warmed with stirring at 130° C. for 5 minutes. Cupric hydroxide (15.4 g, 0.147 mol) was added and the reaction was maintained at this temperature for 1.5 hours. The product was diluted with acetone, filtered and stripped of solvent to afford the final product.

EXAMPLE 5

2,5-Bis(2-methyl-2-hydroxyethylthio)-1,3,4-thiadiazole (93.86 g, 0.35 mol) and heptadecenylsuccinic anhydride (240.0 g, 0.70 mol) were charged to a reaction vessel and heated with stirring at 130° C. for 1.5 hours. The product was filtered while hot.

EXAMPLE 6

2,5-Dimercapto-1,3,4-thiadiazole (10.10 g, 0.067 mol), heptadecenylsuccinic anhydride (50.35 g, 0.148 mol) and diluent oil (25.6 g) were charged to a reaction vessel. Dodecyl glycidyl ether (34.6 g, 0.135 mol) was added slowly with stirring. The reaction mixture was heated at 125° C. for 1 hour.

EXAMPLE 7

2,5-Bis(2-phenoxymethyl-2-hydroxyethylthio)-1,3,4-thiadiazole (123.5 g) and dodecenylsuccinic anhydride (153.0 g) were charged to a reaction vessel and heated with stirring at 135° C. for 1 hour. The product was filtered while hot.

EXAMPLE 8

2,5-Bis(2-butoxymethyl-2-hydroxyethylthio)-1,3,4-thiadiazole (36.5 g, 0.089 mol) and hexadecenylsuccinic anhydride (63.36 g, 0.197 mol) were charged to a reaction vessel and heated with stirring at 130° to 140° C. for 1 hour. A clear product was obtained.

EXAMPLE 9

The product of Example 7 (176 g), calcium oxide (16 g) and water (3 g) were charged to a reaction vessel and heated at 100° C. for 1 hour. Thereafter, the reaction temperature was raised to 150° C. to purge off water. The product was filtered while hot.

EXAMPLE 10

2,5-Bis(2-butoxymethyl-2-hydroxyethylthio)-1,3,4-thiadiazole (31.5 g, 0.076 mol) and polyisobutene ($C_{22}$) succinic anhydride (75.95 g, 0.16 mol) were charged to a reaction vessel and heated with stirring at 130° to 140° C. for 1 hour. A clear product was obtained.

EXAMPLE 11

1. Shell Four-Ball Wear Test

The test was conducted essentially according to the method described in ASTM D-2266 procedure. Four highly polished steel balls 12.5 mm in diameter were placed in a test cup and submerged in the test sample. The test oil was Sunvis ™ 21 manufactured by Sun Oil Company. The test was carried out at a rotation speed of 1800 rpm under a load of 20 kg at 54.5° C. for 60 minutes. The diameter of wear scar produced by samples containing additives of the invention was measured and the data compiled in Table I. The data indicate that the present additives have excellent antiwear properties.

TABLE I

Four-ball Wear Test

| Sample | Additive | Percent | Scar Diameter, mm 20 kg |
|---|---|---|---|
| 1 | None | — | 0.70 (av.) |
| 2 | 2,5-Bis(2-butoxymethyl-2-hydroxyethylthio)-1,3,4-thiadiazole bis half ester with polyisobutyl (C$_{22}$) succinic acid | 0.5 | 0.35 |
| 3 | 2-(2-Dodecyloxymethyl-2-hydroxyethylthio)-5-mercapto-1,3,4-thiadiazole mono half ester with polyisobutyl (C$_{22}$)-succinic acid | 0.5 | 0.56 |
| 4 | 2-(2-Butoxymethyl-2-hydroxy-ethylthio)-5-(2-hydroxy-4-mono half ester with heptadecylsuccinic acid | 0.5 | 0.41 |
| 5 | 2-(2-Butoxymethyl-2-hydroxy-ethylthio)-5-(2-pinylthio)-1,3,4-thiadiazole mono half ester with dodecylsuccinic acid | 0.5 | 0.39 |
| 6 | 2,5-(2-Hydroxyethylthio)-1,3,4-thiadiazole bis half ester with polyisobutyl (950 mol. wt.) succinic acid mono calcium salt | 2.5 | 0.46 |

EXAMPLE 12

Copper Corrosion Test

The compounds of the invention were evaluated as copper inhibitors by the copper strip tarnish test according to ASTM D-130 in oil media. A standard copper strip was placed in a test tube containing the test sample and heated on a water bath at 100° C. After heating oil samples for 3 hours, the strips were evaluated for corrosion by comparing with standard ASTM copper strips. A rating of 1A indicates no corrosivity, 1B to 3B indicates slight to dark tarnish, while a rating of 4A to 4C denotes corrosion. The base oil was a blend of Exxon 150 SNO and Bright Stock and contained 3 percent of copper corrosion inducer.

The results compiled in Table I below show that samples 8 and 9 containing compounds of the invention impart good corrosion protection as compared to sample 7 oil blend containing no corrosion inhibiting additive.

TABLE II

Copper Corrosion Test

| Sample | Additive | Percent | 3 hrs. | 24 hrs. |
|---|---|---|---|---|
| 7 | None | — | 3A | — |
| 8 | Product Example 3 | 0.5 | 1B | 1B |
| 9 | Product Example 3 | 0.25 | 1B | 1B |

EXAMPLE 13

Rust Inhibition Test

Rust inhibition of grease samples 10 to 13 was evaluated by the ASTM D-1743 method and of oil samples 14, 15 and 16 by the ASTM D-665 method.

The test grease was a commercial lithium stearate grease (Li-OH Stearate grease manufactured by Witco Co.). The test oil was that of example 12. All samples including controls contained 3 percent of rust promoter. The results compiled in Table III show that grease samples 11 to 13 containing additives of the invention show good rust inhibition in grease. Sample 15 of the invention show good rust inhibition in oil.

TABLE III

Rust Inhibition Test

| Sample | Additive | Percent | D-1743 | D-665 Sequence A | B |
|---|---|---|---|---|---|
| 10 | None | — | Fail | | |
| 11 | Product Example 1 (50% active) | 2.0 | Pass | | |
| 12 | Product Example 2 (75% active) | 1.35 | Pass | | |
| 13 | Product Example 3 | 3.0 | Pass | | |
| 14 | None | — | | Fail | Fail |
| 15 | Product Example 3 | 0.1 | | Pass | Pass |

EXAMPLE 14

Oxidation Inhibition Test

The oxidation resistance of lubricating grease samples 16, 17, and 18 was determined by ASTM D-942 method and lubricating oil samples 19 and 20 by the ASTM D-2272 method.

The grease samples were oxidized in a bomb heated to 99° C. and filled with oxygen at 100 psi (758 kPa). Pressure was observed at intervals stated in Table IV. The degree of oxidation after a given period of time was determined by the corresponding decrease in oxygen pressure. Lithium stearate grease was used as the base grease.

The oil samples were placed in a bomb together with water and a copper catalyst coil. The bomb was charged with oxygen to a pressure of 90 psi (620 kPa) and heated at 150° C. and 100 rpm. The number of minutes required to reach a specific drop in gage pressure is the oxidation stability of the test sample. Exxon 1000 SUS was used as the base oil. The results are compiled in Table IV.

TABLE IV

Oxidation Inhibition

| Sample | Additive | Percent | D-942 Oxygen, psi 100 hrs. | 200 hrs. | 500 hrs. | D-2272 Min. to Pressure Drop |
|---|---|---|---|---|---|---|
| 16 | None | — | >50 | — | — | — |
| 17 | Example 1 (50% active) | 3.0 | 5 | 10 | 20 | — |
| 18 | Example 3 | 2.0 | 2 | 5.5 | 14.5 | — |
| 19 | None | — | — | — | — | 14.5 |
| 20 | 2,5-Bis(2-hydroxy-ethylthio)-1,3,4-thiadiazole bis half ester with polyisobutyl (950 mol. | 2.5 | — | — | — | 217.5 |

TABLE IV-continued

| | | Oxidation Inhibition | | | D-2272 Min. to Pressure Drop |
|---|---|---|---|---|---|
| | | | D-942 Oxygen, psi | | |
| Sample | Additive | Percent | 100 hrs. | 200 hrs. | 500 hrs. | |
| | wt.) succinic acid mono calcium salt | | | | | |

The above embodiments have shown various aspects of the present invention. Other variations will be evident to those skilled in the art and such modifications are intended to be within the scope of the invention as defined by the appended claims.

What is claimed is:

1. A compound having the structural formula

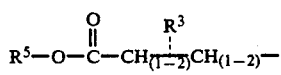

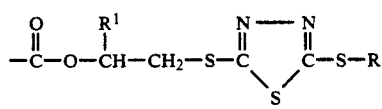

wherein R represents hydrogen, $C_{1-100}$-alkyl, alkenyl, cycloalkyl, alkylcycloalkyl, 2-hydroxyalkyl and a group of the structural formula

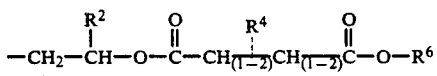

and wherein $R^1$ and $R^2$ are selected independently from the group consisting of $C_{1-50}$-alkyl, alkoxyalkyl, phenoxyalkyl, aralkyl, cycloalkyl, aryl, alkaryl, alkenyl and alkynyl groups, $R^3$ and $R^4$ are selected independently from the group consisting of $C_{1-50}$-alkyl, aralkyl, cycloalkyl, aryl, alkaryl, alkenyl and alkynyl groups, $R^5$ is calcium ion and $R^6$ is calcium ion or hydrogen.

2. A composition comprising a major amount of oil of lubricating viscosity wherein said oil is a petroleum hydrocarbon oil or a synthetic oil and from about 0.1 to 12 percent by weight of a compound having the structural formula

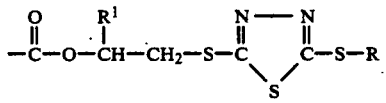

wherein R represents hydrogen, $C_{1-100}$-alkyl, alkenyl, cycloalkyl, alkylcycloalkyl, 2-hydroxyalkyl and a group of the structural formula

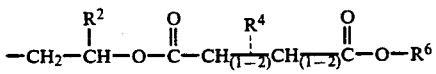

and wherein $R^1$ and $R^2$ are selected independently from the group consisting of $C_{1-50}$-alkyl, alkoxyalkyl, phenoxyalkyl, aralkyl, cycloalkyl, aryl, alkaryl, alkenyl and alkynyl groups, $R^3$ and $R^4$ are selected independently from the group consisting of $C_{1-50}$-alkyl, aralkyl, cycloalkyl, aryl, alkaryl, alkenyl and alkynyl groups, $R^5$ is calcium ion and $R^6$ is calcium ion or hydrogen.

3. A composition according to claim 2 which further contains a thickening agent.

4. A composition comprising at least 40 percent by weight of water, from 0 to 15 percent by weight of petroleum hydrocarbon oil or synthetic oil and about 0.1 to 10 percent by weight of a compound having the structural formula

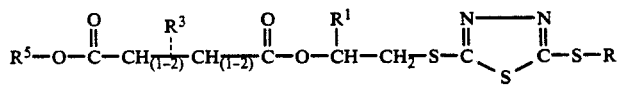

wherein R represents hydrogen, $C_{1-100}$-alkyl, alkenyl, cycloalkyl, alkylcycloalkyl, 2-hydroxyalkyl and a group of the structural formula

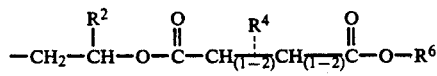

and wherein $R^1$ and $R^2$ are selected independently from the group consisting of $C_{1-50}$-alkyl, alkoxyalkyl, phenoxyalkyl, aralkyl, cycloalkyl, aryl, alkaryl, alkenyl and alkynyl groups, $R^3$ and $R^4$ are selected independently from the group consisting of $C_{1-50}$-alkyl, aralkyl, cycloalkyl, aryl, alkaryl, alkenyl and alkynyl groups, $R^5$ and $R^6$ are selected independently from the group consisting of hydrogen, metal cation and trialkylammonium.

5. A composition comprising a major amount of alcohol fuel and from about 0.01 to 2 percent by weight of a compound having the structural formula

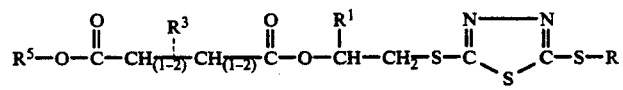

wherein R represents hydrogen, $C_{1-100}$-alkyl, alkenyl, cycloalkyl, alkylcycloalkyl, 2-hydroxyalkyl and a group of the structural formula

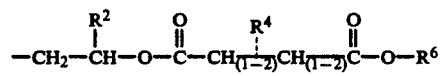

and wherein $R^1$ and $R^2$ are selected independently from the group consisting of $C_{1-50}$-alkyl, alkoxyalkyl, phenoxyalkyl, aralkyl, cycloalkyl, aryl, alkaryl, alkenyl and alkynyl groups, $R^3$ and $R^4$ are selected independently from the group consisting of $C_{1-50}$-alkyl, aralkyl, cycloalkyl, aryl, alkaryl, alkenyl and alkynyl groups, $R^5$ and $R^6$ are selected independently from the group consisting of hydrogen, metal cation and trialkylammonium.

* * * * *

UNITED STATES PATENT AND TRADEMARK OFFICE
CERTIFICATE OF CORRECTION

PATENT NO. : 5,177,213
DATED : Jan. 5, 1993
INVENTOR(S) : Thomas J. Karol

It is certified that error appears in the above-identified patent and that said Letters Patent is hereby corrected as shown below:

At Col. 5, Table I, Line 26, Sample 4

" 2-(2-Butoxymethyl-2-hydroxy-ethylthio)-
5-(2-hydroxy-4-mono half ester with
heptadecylsuccinic acid"  should be
-- 2-(2-Butoxymethyl-2-hydroxyethylthio)-
5-(2-hydroxy-4-oxaoctyl)-1,3,4-
thiadiazole mono half ester with
heptadecylsuccinic acid --.

Signed and Sealed this

Twenty-sixth Day of October, 1993

Attest:

BRUCE LEHMAN

*Attesting Officer*    *Commissioner of Patents and Trademarks*